(12) United States Patent  
Raab

(10) Patent No.: US 6,413,212 B1
(45) Date of Patent: Jul. 2, 2002

(54) METHOD AND APPARATUS FOR WOUND MANAGEMENT

(75) Inventor: Simon Raab, Longwood, FL (US)

(73) Assignee: Faro Technologies, Inc., Lake Mary, FL (US)

( * ) Notice: Subject to any disclaimer, the term of this patent is extended or adjusted under 35 U.S.C. 154(b) by 0 days.

(21) Appl. No.: 09/401,244

(22) Filed: Sep. 23, 1999

Related U.S. Application Data

(63) Continuation of application No. 08/733,700, filed on Oct. 17, 1996, now Pat. No. 5,957,837.

(51) Int. Cl.[7] .............................................. A61B 5/00
(52) U.S. Cl. ........................................ 600/300; 600/587
(58) Field of Search ................................ 600/300, 407, 600/409; 382/128

(56) References Cited

U.S. PATENT DOCUMENTS

| 4,483,075 A | 11/1984 | Kundin |
| 4,576,177 A | 3/1986 | Webster, Jr. ................ 128/660 |
| 4,771,774 A | 9/1988 | Simpson et al. ............ 128/305 |
| 5,082,001 A | * 1/1992 | Vannier et al. ......... 340/324 R |
| 5,082,003 A | 1/1992 | Lamb et al. |
| 5,102,391 A | 4/1992 | Palestrant .................... 604/116 |
| 5,230,623 A | 7/1993 | Guthrie et al. |
| 5,347,256 A | 9/1994 | Yumiki et al. ................ 336/84 |
| 5,359,312 A | 10/1994 | Choi ........................... 336/84 |
| 5,402,582 A | 4/1995 | Raab |
| 5,588,428 A | * 12/1996 | Smith et al. ................ 382/128 |
| 5,701,902 A | * 12/1997 | Vari et al. ................... 600/545 |

* cited by examiner

Primary Examiner—Francis J. Jaworski
(74) Attorney, Agent, or Firm—Cantor Colburn LLP

(57) ABSTRACT

A wound management system including a measuring device and a computer database system for collecting, managing and displaying wound data. The computer database allows the operator to collect data regarding various wound parameters including perimeters, depth, undermining, and tunneling. As the operator collects wound data, the locations of previous wound data are displayed so that an effective comparison can be made between past and current measurements, The wound management system generates graphical displays that allow the practitioner to quickly track wound healing.

15 Claims, 19 Drawing Sheets

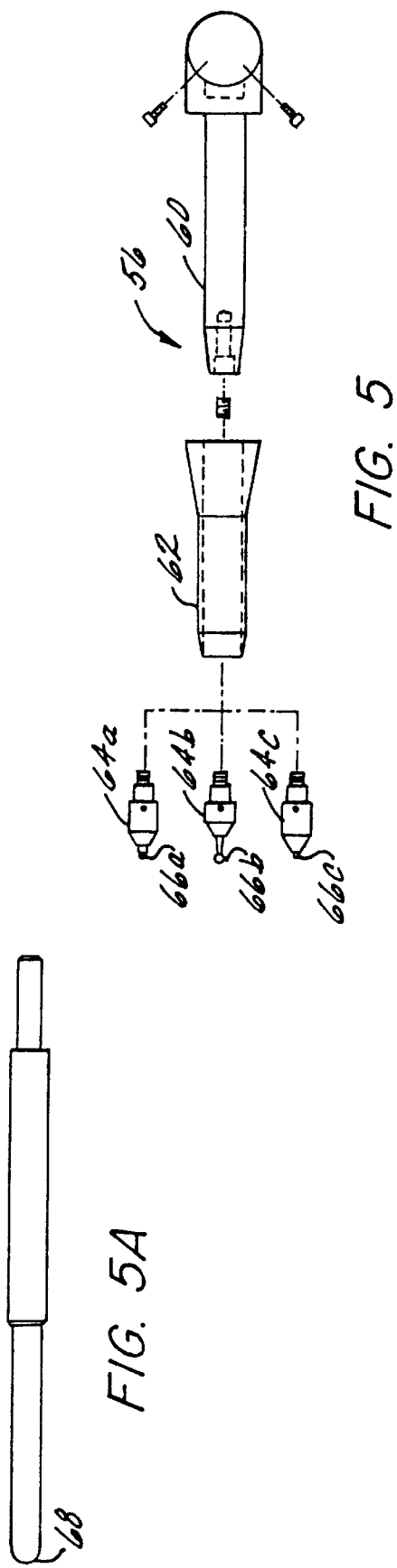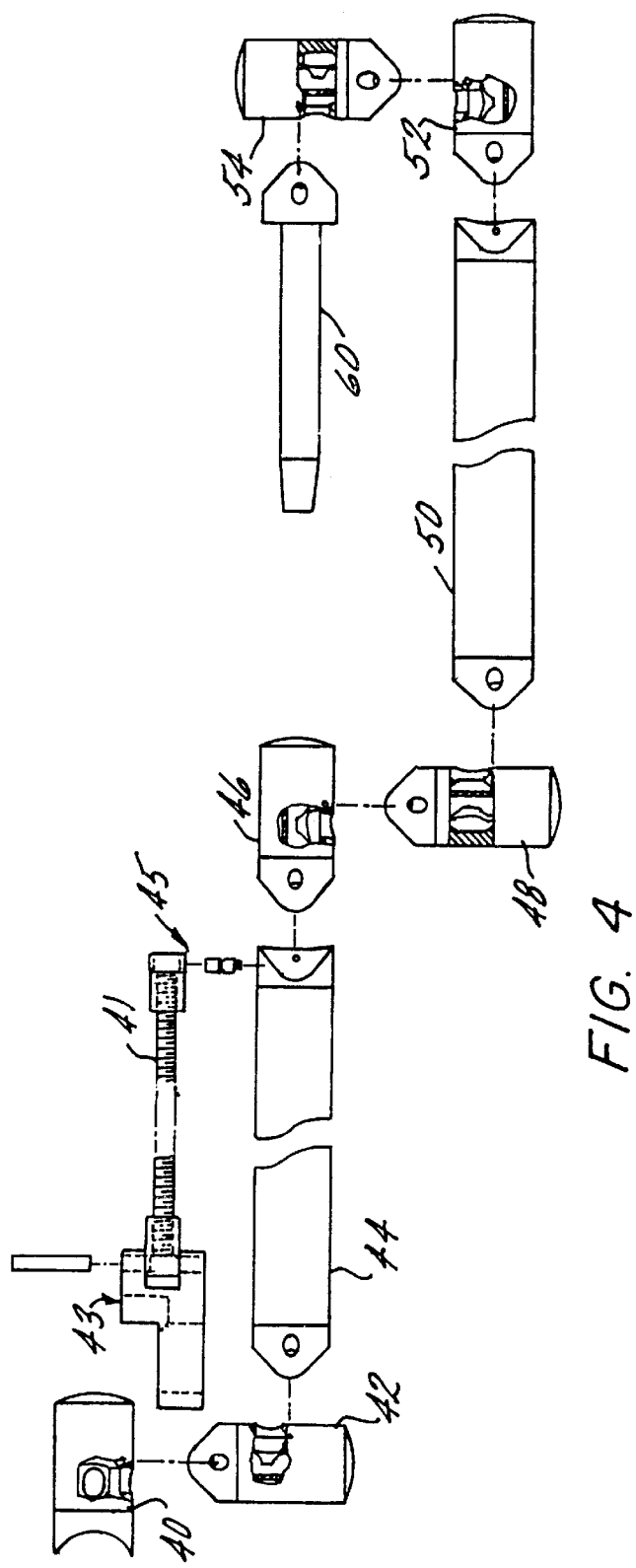
FIG. 5
FIG. 5A
FIG. 4

General Information

First Name: John  MI: Q  Last Name: Public

Occupation: mechanical engineer

Employer: Bell Laboratories

Insurance Co.: Liberty Mutual

Full Address: P.O. Box 1103, Boston MA 06821

Phone: 800-555-1111  Policy No.: 900-2183-083P

Physician Name: Dr. Stanley Ripke

Physician Phone: 600-555-3214

[OK] [Cancel] [Help]

FIG. 8   — 32

Wound Location

Ulcer Location: lateral malleolus

Duration: 2 months

Ulcer Side:
● Left
○ Right

Smoker ● YES ○ No

Years: 15

Amount: 1 p/d

Ulcer Type:
● Venous
○ Pressure

Current Diseases: hypertension

Current Meds: seldane bid, lotrax bid

[OK] [Cancel] [Help]

FIG. 9   — 34

Wound Site

Epithelialization
- Y ●    N ○
- Percent: 0-20%

Exudate
- Y ●    N ○
- Volume: mild
- Color: clear to cloud
- Consistency: liquid
- Odor: light

- Y ○    N ●    Sensory Deficit
- Y ●    N ○    Pain
- Y ●    N ○    Granulation
- Y ○    N ●    Infection
- Y ○    N ●    Necrotic Tissue

[More]

FIG. 10

Lower Limb Area

| | Unaffected | Affected |
|---|---|---|
| Circumference of Limb 10cm below knee | 28 cm | 27 cm |
| Circumference of Limb 3cm above ankle | 18 cm | 19 cm |
| Texture of Skin | normal | normal |
| Hair Distribution | normal | sparse |
| Toe Nails | OK | OK |
| Color of Feet | pink | pink |
| Temperature of Feet (to touch) | warm | warm |
| Ankle-Brachel Index (ABI) | 1.89 | 1.74 |

[More] [Back]

FIG. 11

| Advanced Diagnostics | | 40 |
|---|---|---|
| Ptc O2-Ulcer Rim | 14 | Notes: |
| Ptc O2-Ulcer Chest | 80 | Wound is healing well, but not as fast as initially expected. Patient compliance is contributing factor to this. |
| Ptc O2-Mirror Ulcer | 59 | |
| Ptc O2-Dorsum | 51 | |
| Ptc O2-Healthy Skin | 54 | |
| Ptc CO2 | 68 | |
| Perimed (PU) | 2.4 | |
| Laserflo (ml/min/100g) | 3.02 | |
| O2 Saturation | 97 | |
| HR (beats/min) | 71 | |

[ OK ]  [ Back ]  [ Cancel ]

*FIG. 12*

Select Preferred Scoring System
- ● Norton Scale
- ○ Braden Scale
- ○ Gosnell Scale

[ OK ]  [ Cancel ]  [ Help ]

*FIG. 13*

Norton Scale

Physical Condition
- ○ Good
- ◉ Fair
- ○ Poor
- ○ Very Bad

Mental State
- ○ Alert
- ◉ Apathetic
- ○ Confused
- ○ Stupor

Activity
- ○ Ambulant
- ◉ Walks w/Assit
- ○ Chairbound
- ○ Bed

Mobility
- ○ Full
- ◉ Some Limited
- ○ Very Limited
- ○ Immobile

Incontinence
- ◉ Not
- ○ Occasional
- ○ Usually Urine
- ○ Double Incontinent

Score: 16 — 42

OK   Cancel   Help

*FIG. 14*

Braden Scale

Sensory Perception
- ○ Totally Limited
- ○ Very Limited
- ◉ Slightly Limited
- ○ No Impairment Noisture
- ○ Constantly Moist
- ○ Moist
- ○ Occasionaly Moist
- ◉ Rarely Moist Mobility
- ○ No Mobility
- ○ Very Limited
- ◉ Slightly Limited
- ○ No Limitation Activity
- ○ Bedfast
- ○ Chairfast
- ◉ Walks Occasionaly
- ○ Walks Frequently Nutrition
- ○ Very Poor
- ○ Inadequate
- ◉ Adequate
- ○ Excellent Friction and Shear
- ○ Problem
- ◉ Potention Problem
- ○ No Problem Score: 11   44

OK   Back   Cancel

*FIG. 15*

Gosnell Scale

Menbility
- ○ Full
- ● Some Limited
- ○ Very Limited
- ○ Immobile

Activity
- ○ Ambulant
- ● Walks w/Assit
- ○ Chairfast
- ○ Bedfast

Continence
- ○ Full Control
- ● Usual Control
- ○ Minimal Control
- ○ No Control

Mental State
- ● Alert
- ○ Apathetic
- ○ Confused
- ○ Stupor
- ○ Unconscious

Nutrition
- ● Good
- ○ Fair
- ○ Poor

Score

17 — 46

[ OK ] [ Cancel ] [ Help ]

*FIG. 16*

Select Kundin Calculation Method

- ● WMS Auto Entry
- ○ Manual Data Entry

[ OK ] [ Cancel ] [ Help ]

Lab Workup

Blood
- Urea N: 10 mg/dl
- Creatinine: 10 gm/kg
- Cholesterol: 10 mg/dl
- LDH: 10 u/L
- Na: 10 mg/dl
- K: 10 mg/dl
- HGB: 10 gm/dl
- HCT: 10 %
- PLT: 10 %10e3
- Ca: 10 mg/dl
- Ph: 10 mg/dl
- Glucose: 10 mg/dl
- Chloride: 10 mg/dl
- Total Protein: 10 gm/dl
- Albumin: 10 gm/dl Urine
- Spec Gravity: 10
- pH: 10
- WBC: 10 /ml
- RBC: 10 /ml
- HBG: 10 /ml

[OK] [Cancel] [Help]

FIG. 23

WMS Measurements — 50

[Done] [Cancel] [Help]   X : 18.00   Y : 26.11   Z : 5.56

- 51 — Perim
- 52 — Under
- 53 — Tunnel
- 54 — Depth
- 55 — Backup
- 56 — Save
- 57 — Print

60

Digitize a point outside the lower left hand corner of the wound — 62

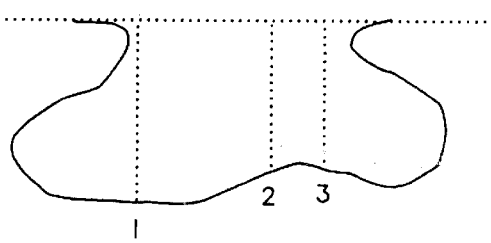
FIG. 35
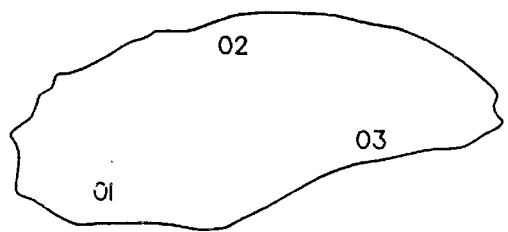
FIG. 36
FIG. 37
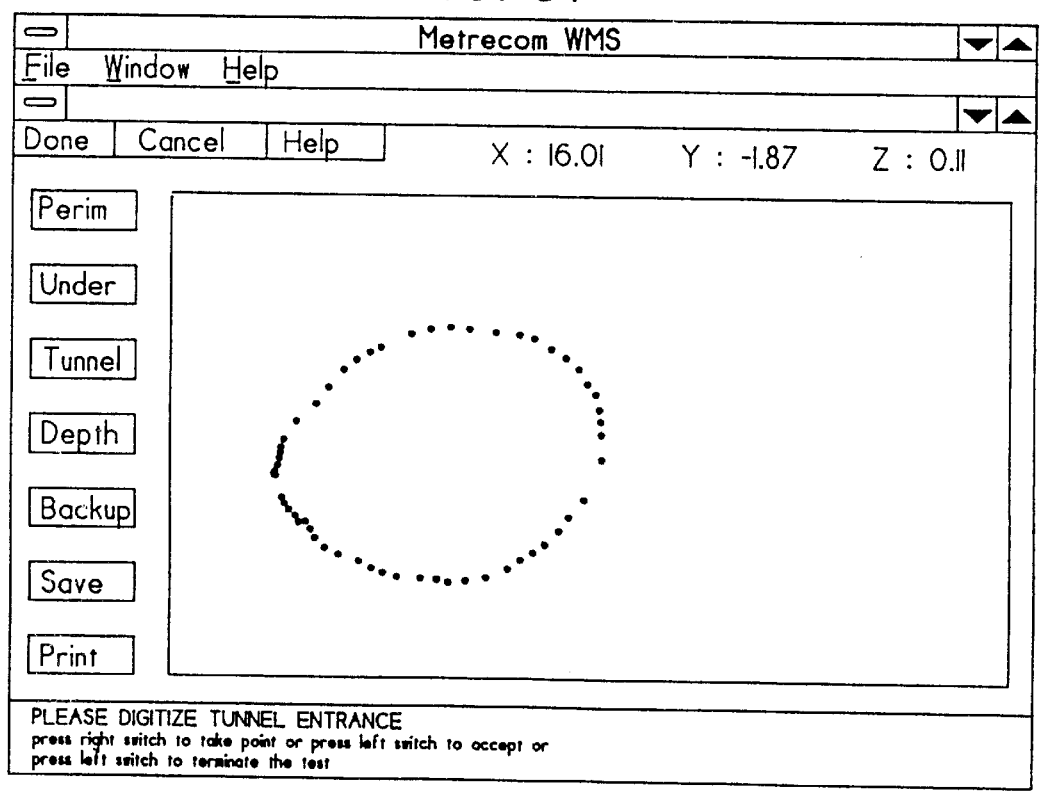

METHOD AND APPARATUS FOR WOUND MANAGEMENT

CROSS-REFERENCE TO RELATED APPLICATIONS

This application is a continuation of U.S. patent application Ser. No. 08/733,700 filed Oct. 17, 1996, U.S. Pat. No. 5,957,837 entire contents of which are incorporated herein by reference.

BACKGROUND OF THE INVENTION

1. Field of the Invention

The invention relates to the field of evaluative medicine. More particularly, the invention relates to a method of using a coordinate measuring machine for physical measurement of three dimensional wounds in a body. The wound data is incorporated in a database along with physiological attributes of the patient to provide a powerful tool for wound analysis.

2. Prior Art

In the field of medical technology advancements in treatment and methods evaluating the effectiveness thereof are continually sought in a variety of areas. One very common area of improvement is in the use of computers for a variety of applications.

One such system is that taught in U.S. Pat. No. 5,230,623 to Guthrie et al wherein a power arm is linked to a computer and display. Arm position and joint angles in the arm are assimilated and utilized to provide an image on the display of where the pointer is relative to the patient. The pointer can also be utilized as a three-dimensional mouse to allow a surgeon to interact with the display.

Another computer based system is described in U.S. Pat. No. 5,082,003 to Lamb et al. Lamb et al measures inter-skeletal distances during relative movement between skeletal bodies. The signal produced by the articulated linkage is translated into a measurement of distance between tips of the first and second skeletal bodies.

Other systems exist, however, there is no system in the prior art for measuring the positional, orientational, dimensional and volumetric coordinates of a wound on a body. This type of system has been the subject of long felt need as physicians attempt to evaluate the effectiveness of a given treatment in healing a three dimensional wound.

Of particular concern is the treatment of geriatric patients afflicted with decubitus ulcers. Decubitus ulcers are common in bed ridden patients of all ages. These ulcers are a symptom of a particular area of the body pressing against a bed for an extended period of time. The area can be any part of the body, one common example being the buttocks of the patient. Another form of common ulcer is a Venous ulcer often found in diabetics due to poor peripheral circulation.

Decubitus ulcers are a particularly vexatious condition both to patients and their physicians because they are difficult to treat successfully, and even more difficult to evaluate relative to the effectiveness of any particular treatment. Decubitus ulcers are slow to heal and without evaluative methods require excessively long periods of time before any visible sign of healing can be perceived. No prior art device to date has offered a suitable solution.

SUMMARY OF THE INVENTION

The above-discussed and other drawbacks and deficiencies of the prior art are overcome or alleviated by the wound management system of the present invention. The wound management system includes a measuring device and a computer database system for collecting, managing and displaying wound data. The computer database allows the operator to collect data regarding various wound parameters including perimeters, depth, undermining, and tunneling. As the operator collects wound data, the locations of previous wound data are displayed so that an effective comparison can be made between past and current measurements. The wound management system generates graphical displays that allow the practitioner to quickly track wound healing.

The above-discussed and other features and advantages of the present invention will be appreciated and understood by those skilled in the art from the following detailed description and drawings.

BRIEF DESCRIPTION OF THE DRAWINGS

Referring now to the drawings wherein like elements are numbered alike in the several FIGURES:

FIG. 4 is an exploded view of a multi-jointed arm;

FIG. 5 is an exploded view of the arm tip and assorted probe ends;

FIG. 5A is a side view of an alternative probe tip;

FIG. 8 is an illustration of a second patient information screen;

FIG. 9 is an illustration of a wound location identification screen

FIG. 10 is an illustration of a first assess screen;

FIG. 11 is an illustration of a second assess screen;

FIG. 12 is an illustration of a third assess screen;

FIG. 13 is an illustration of a score selection screen;

FIG. 14 is an illustration of a Norton scoring screen;

FIG. 15 is an illustration of a Braden scoring screen;

FIG. 16 is an illustration of a Gosnell scoring screen;

FIG. 17 is an illustration of a Kundin calculation selection screen;

FIG. 20 is an illustration of an automatic Kundin scoring screen;

FIG. 21 is an illustration of a manual Kundin scoring screen;

FIG. 22 is an illustration of a lab work screen;

FIG. 23 is an illustration of a wound management system measurement screen;

FIG. 35 is a side view of a wound illustrating wound depth measurements;

FIG. 36 is a top view of a wound illustrating wound depth measurements;

FIG. 37 is an illustration of a wound depth digitizing screen;

DETAILED DESCRIPTION OF THE INVENTION

Figure 1:
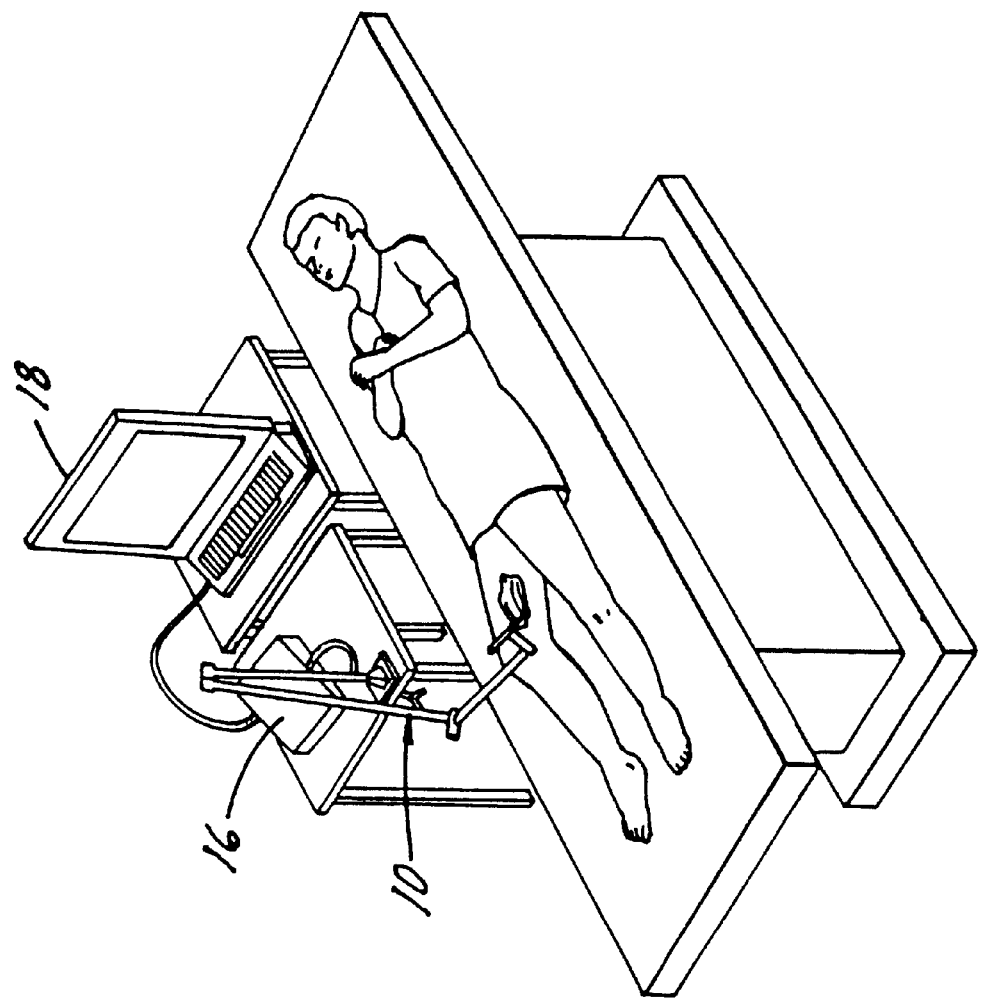
FIG. 1 is a diagrammatic view of the wound management system and a patient.

Referring to FIG. 1, a three dimensional measuring system for use in the present invention generally comprises a coordinate measuring machine (CMM) 10 composed of a manually operated multijointed arm 12 and a support base or post 14 (shown in FIG. 2), a controller or serial box 16 and a computer 18. It will be appreciated that CMM 10 electronically communicates with serial box 16 which, in turn, electronically communicates with computer 18. In an alternative embodiment, the circuitry within the serial box 16 is located within the base 14 thereby eliminating the need for a separate serial box 16. In an exemplary embodiment, computer 18 is a laptop PC to facilitate movement of the wound measurement system.

The CMM 10 includes transducers (e.g., one transducer for each degree of freedom) which gather rotational positioning data and forward this basic data to serial box 16. Serial box 16 provides a reduction in the overall requirements of host computer 18 to handle certain complex calculations and provides certain preliminary data manipulations. Basic transducer data is sent from CMM 10 to serial box 16. Serial box 16 then processes the raw transducer data on an ongoing basis and responds to the queries of the host computer with the desired three-dimensional positional or orientational information.

To ensure that multiple measurements are accurate, the CMM 10 should be firmly attached to a sturdy object (e.g. a table). A clamp may be affixed to the object and the base 14 of the CMM to prevent the CMM 10 from moving while taking wound measurements. This allows the wound measurement system to be portable and easily taken to the patient. Accordingly, patients are not disturbed by being required to move from their individual rooms to a wound measurement area.

Figure 3:
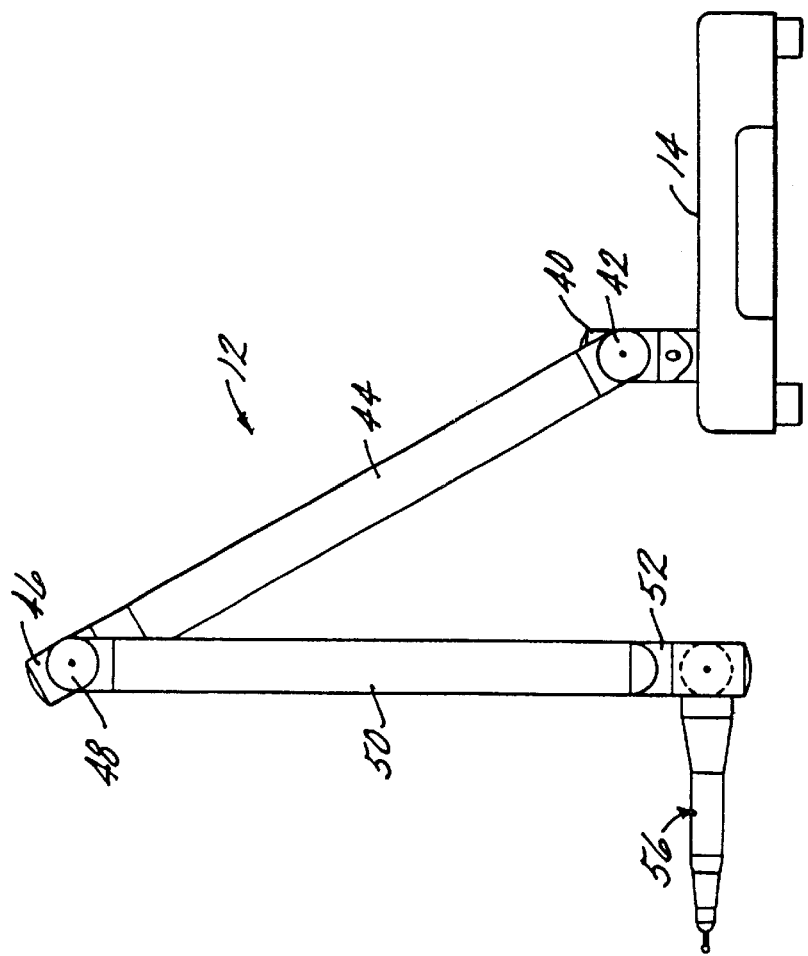
FIG. 3 is a front view of the coordinate measuring machine.
Figure 2:
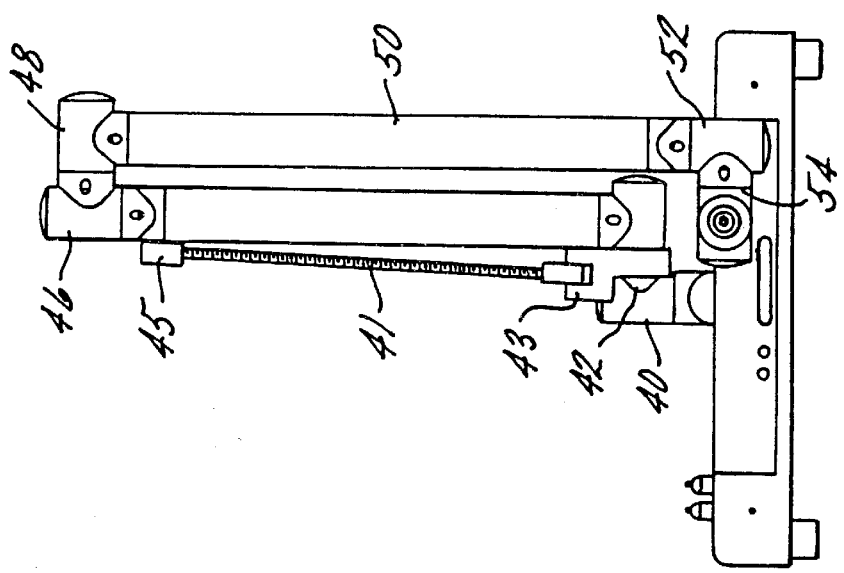
FIG. 2 is a side view of the coordinate measuring machine.

As best shown in FIGS. 2 and 3, the CMM 10 comprises a base 14 connected to a first transfer housing 40 which, in turn, is connected to a second transfer housing 42 (positioned transverse to housing 40). A first extension member 44 is rigidly attached to a second set of two transfer housings including a third transfer housing 46 trangversely attached to a fourth transfer housing 48. First extension member 44 is positioned perpendicularly between transfer housings 42 and 46. A second extension member 50 is aligned with an rigidly attached to transfer housing 48. Rigid extension member 50 is rigidly attached to a third set of two transfer housings including a fifth transfer housing 52 transversely attached to a sixth transfer housing 54. Fifth transfer housing 54 has attached thereto a probe assembly 56. A spring 41 is provided along the length of the first extension member 44 to facilitate positioning the CMM 10. A spring bracket 43 connects the spring 41 to the second transfer housing 42 and a spring mounting assembly 45 connects the other end of the spring 41 to the distal end of the first extension member 44.

FIG. 4 is an exploded view of the arm 12. As shown in FIG. 4, the arm 12 includes six transfer housings 40, 42, 46, 48, 52 and 54. The first extension member 44 is positioned between the second transfer housing 42 and third transfer housing 46. The second extension member is positioned between the fourth transfer housing 48 and the fifth transfer housing 52. An probe assembly inner sleeve 60 is connected to the sixth transfer housing 54.

FIG. 5 is an exploded view of the probe assembly 56. As previously described, the probe assembly includes an inner sleeve 60 that is connected to the sixth transfer housing 54. An outer sleeve 62 fits over the inner sleeve and receives a variety of probing devices. The probing devices include a probe body 64a–c and a probe tip 66a–c. The probe body 64a–c includes threads at one end to engage threads formed in the outer sleeve 62. This allows the type of probe to be exchanged with ease. FIG. 5A is an alternative probe tip having a half spherical tip 68.

The CMM 10 allows measurement in three dimensional space to collect information, described in detail below, regarding a patient's wound. While the above generally describes the CMM 10, additional details of the CMM 10 are found in U.S. Pat. No. 5,402,582 which is incorporated herein by reference. The method of using the CMM 10 in conjunction with the wound management system of the present invention will now be described.

The wound management system (WMS) of the present invention is comprised of two major elements: the CMM 10 and a computer database system. The CMM 10 is used for physical measurement of wound characteristics such as perimeter, wound area, wound depth, undermining, tunneling, and other attributes associated with the dimensional characteristics of a wound. This data is accumulated directly into a specially designed database program. The database program is preferably structured in a graphics based user interface (e.g. Microsoft Windows®) to facilitate operation. This wound data includes the dimensional data mentioned above, as well as all other physiological attributes of the patient relating to the wounds including both conventional objective and subjective evaluations.

The computer database system is designed to be executed on a general purpose computer such as the laptop computer 18 shown in FIG. 1. The present invention can also be embodied in the form of computer program code embodied in tangible media, such as floppy diskettes, CD-ROMs, hard drives, or any other computer-readable storage medium, wherein, when the computer program code is loaded into and executed by a computer, the computer becomes and apparatus for practicing the invention. The present inventions can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention.

Perhaps one of the greatest difficulties in the assessment of wound care is the slow progress of healing and the difficulty in defining the rate of success over time. The database has been structured specifically to represent any one of the variables discussed in a graphical, time-based format so that healing trends become immediately apparent to the practitioner who determines whether or not the current treatment plan is effective.

Figures 6, 7:
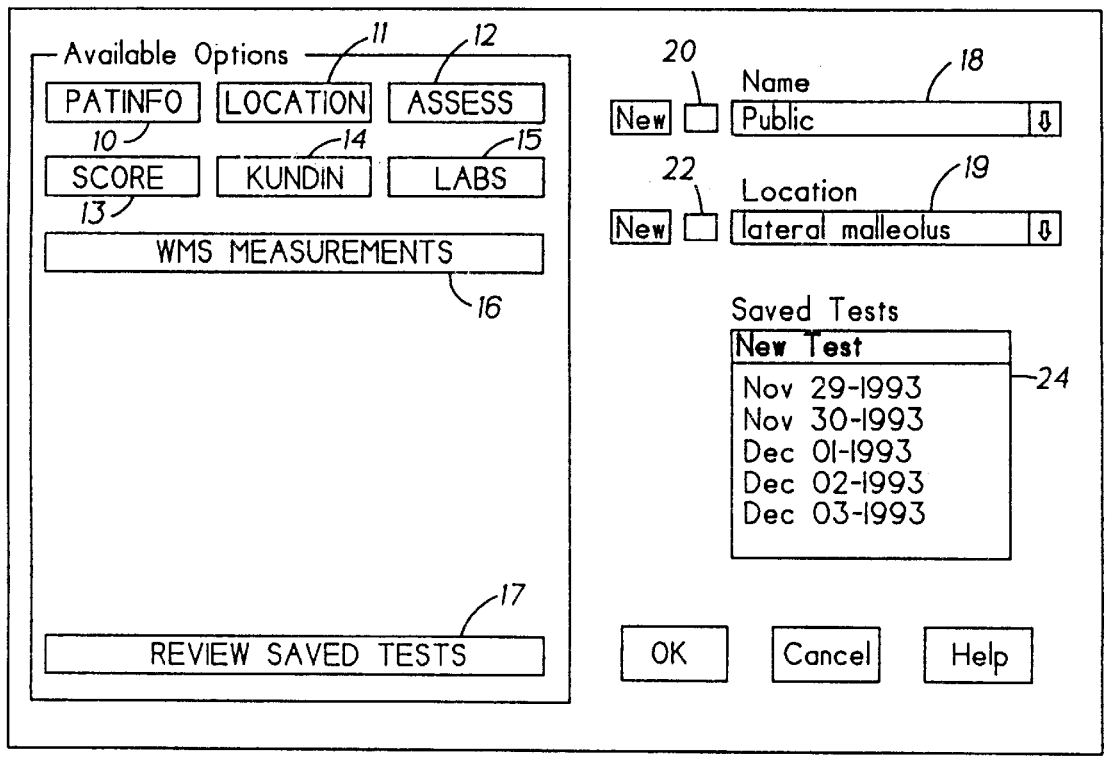
FIG. 6 is an illustration of the main dialog screen.
FIG. 7 is an illustration of a first patient information screen.

FIG. 6 is a screen display illustrating the main dialog screen of the wound management database. From the main dialog screen all other areas are accessible as will be described herein. Adding and selecting patients, choosing which test is to be performed and indicating what data is input as part of the patient's wound assessment are all accessed from the main dialog screen. The main dialog screen of FIG. 6 includes "buttons" 10–17 labeled Patinfo, Location, Assess, Score, Kundin, Labs, WMS Measurements and Review Saved Tests. The buttons are "pressed" using an input device such as a keyboard or a mouse. The functions associated with each of these buttons are described below.

Before beginning any testing, the operator must first select a patient record from the patient list area 18. If a series of patient records are available, the patient name list 18 is scrolled through and the desired name is selected by either using the mouse or cursor keys. If the patient to be tested does not have an existing record, the operator creates a new record checking the new patient check box 20 located immediately to the left of the patient name list 18. Checking the new patient check box 20 will direct flow of the program to the first of the two patient information screens shown in FIGS. 7 and 8.

As shown in FIG. 7, patient information is entered in the spaces provided. The user may use the keyboard or mouse to move from one entry to the next. Once the first screen of patient information is completed, the user clicks the More button 30, or presses ENTER, to proceed to the second patient information screen shown in FIG. 8. Once all the patient information has been entered, the user selects the Ok button 32 or presses ENTER to proceed. Since this is a new record (which has not been associated with any wound locations), the system will be led directly to a blank wound location screen shown in FIG. 9 where the operator is required to enter information on the new patient's wound site. Once all the wound information has been entered, the operator clicks the Ok button 34 or presses the ENTER to return to the main dialog screen. The patient name and wound location that have been entered are highlighted, and the operator may now proceed with testing.

Prior to performing any testing, the operator must select a patient name and a wound location. If the wound location has been entered, the operator selects the wound site from the list of patient's wounds located in the wound location list 19. A patient may have as few as one site, or as many sites as necessary in the list. The operator may select only one site at a time for testing purposes. If the wound to be tested does not have an existing record, the operator adds a wound location by checking the new wound check box 22 located immediately to the left of the wound location list 19. Checking the new wound location check box 22 will automatically direct the program to the wound site information screen shown in FIG. 9. The operator enters the wound site information in the spaces provided, then either clicks on the More button, or presses ENTER to return to the main dialog screen of FIG. 6. The new wound location that has just been entered is highlighted, and the operator may proceed with testing.

PATINFO

The PATINFO button is used to review or modify the patient information for existing patients. First, a patient name is selected from the patient name list 18. Then, the PATINFO button is pressed to access the first of the two patient information screens shown in FIG. 7. The operator may review/edit the patient information in the first and second patient information screens and return to the main menu as described above.

LOCATION

Pressing the LOCATION button allows the operator to review and/or change the current patient's currently selected wound site information. Upon pressing the LOCATION button 11, the wound location information screen appears as shown in FIG. 9. This screen also contains three standard buttons in the bottom right hand portion of the screen: The Ok button saves the information, and returns to the main dialog screen, the Cancel button does not save any entered or changed information but still returns to the main dialog box, and the Help button will provide help on the wound location information screen.

ASSESS

Pressing the ASSESS button 12 allows the operator to either review the wound assessment information for the current patient and selected wound or to perform a new wound assessment. To perform a new assessment, the operator selects "New Test" in the test list 24 before pressing the ASSESS button 12. To review a saved assessment, the operator selects the test date on which the desired test wag performed in the test list 24 before pressing the ASSESS button 12.

Once the ASSESS button is pressed, the first of the three assessment screens will appear (FIG. 10). This screen contains information pertaining to the wound itself and will either be blank (or default selections) for a new test or contain data from a saved test. The percent of epithelization is entered if appropriate. The exudation of the wound is also classified. In addition, the presence of sensory deficit, pain, granulation, infection and necrotic tissue is noted. It is understood that other wound factors may be used depending upon the preference of the user. For new tests, selections may be made by selecting the appropriate buttons and making combo box selections. When done, the More button is pressed to proceed to the second assessment screen (FIG. 11).

The second assessment screen shown in FIG. 11 is specific to lower lib wounds. Entries are made for both unaffected regions and affected regions. Some of the factors measured are wound circumference of limb 10 cm below knee, wound circumference of limb 3 cm above the ankle, texture of skin, hair distribution, toe nails, color of feet, temperature of feet and ankle-brachal index. Once entries and selections are done, the operator chooses More to proceed to the next assessment screen shown in FIG. 12, or Back to go back to the first assessment screen shown in FIG. 10.

The third assessment screen shown in FIG. 12 is specific to advanced wound diagnostics, and contains a short note field 40. The third and last assessment screen shown in FIG. 12 also contains the standard buttons located in the lower-right hand corner of the window: The Ok button saves the information, and returns back to the main dialog box, the Back button returns back to the first assessment screen, and the Cancel button does not save any entered or changed information but still returns to the main dialog box shown in FIG. 6.

SCORE

The SCORE button 13 shown in FIG. 6 allows the operator to either review a previous score test for the current patient and selected wound or to perform a new score test. To perform a new test, the operator selects New Test in the test list 24 before pressing the SCORE button 13. To review a saved test, the operator selects the test date on which the desired test was performed in the test list 24 before pressing the SCORE button 13.

Pressing the SCORE button 13 directs the program to the score selection screen as shown in FIG. 13. For new tests, the operator selects which scoring system they wish to use and then presses Ok to proceed to the scoring screen (FIGS. 14–16) corresponding to the selected scoring scale. To review an existing test, the operators selects the date on which the test was saved in the main dialog's test list 24, then presses the SCORE button 13. The program displays the scoring system selection screen (FIG. 13) where the operator selects the type of scoring system used to rate this patient initially, and then presses Ok to proceed.

If the selected scoring system does not match the original scoring system, the selected scoring screen will appear blank, with no entries. If this occurs, the operators presses Cancel to return to the main dialog, and then try again.

FIGS. 14–16 are the scoring screens for three scoring systems, namely the Norton Scale (FIG. 14), Gosnell Scale (FIG. 15) and the Braden Scale (FIG. 16). Once the operator has selected an item in all the available categories in your selected scale, choosing the Ok button saves the information, and returns to the main dialog box shown in FIG. 6, choosing Cancel abandons any entered or changed information but still returns to the main dialog box shown in FIG. 6. The Help button provides help on the specific scale being used and what the ratings stand for. As the operator makes item selections, the score in windows 42, 44 or 46 increases or decreases depending on which item was selected. Explanations on how much each item affects the total score can be found in the Help portion of each respective scoring screen. The operator must select an option in each category to receive a final score.

KUNDIN

The KUNDIN button 14 allows the operator to either review a Kundin test for the current patient and selected wound or to perform a new Kundin test. To perform a new test, the operator selects New Test in the test list 24 shown in FIG. 6 before pressing the KUNDIN button 14. To review a saved Kundin test, the operator selects the test date on which the desired test was performed in the test list 24 before pressing the KUNDIN button 14.

Pressing the KUNDIN button 14 will present the operator with the score selection dialog as seen in FIG. 17 below. For new tests, the operator selects which calculation method to use (manual or automatic), and then presses Ok to proceed to the screen corresponding to the selected calculation method. To review an existing test, the operator selects the date on which the test was saved in the main dialog's test list 24, then presses the KUNDIN button. The operator selects the type of calculation method used to perform the test initially, and then presses Ok to proceed. If the entered calculation method and the initial calculation method do not match, the selected screen will appear blank, with no data. If this occurs, the operator presses Cancel to return to the main dialog.

Figure 18:
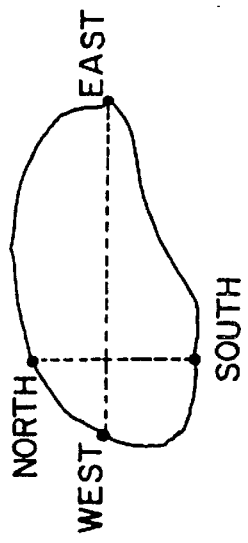
FIG. 18 is a side view of a wound indicating a Kundin depth measurement.
Figure 19:
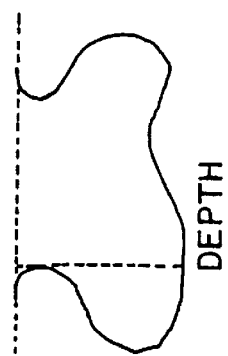
FIG. 19 is a top view of the wound indicating four perimeter points.

Performing a WMS Automatic Kundin calculation involves digitizing up to 5 discrete points in and around the wound. For comparability to the manual method using a Kundin gauge, these five points are labeled North, South, East, West, and Depth, as displayed in FIGS. 18–19. Depth is an optional point to digitize, depending on whether the operator wishes to assess volume of the wound. As in all measurements involving the use of the CMM 10, hygienic precautions are necessary to help avoid introduction of harmful organisms into the wound. Once the operator chooses the WMS Auto Entry selection in FIG. 17, the system prompts the operator to measure the points illustrated in FIGS. 18–19. Once the required points have been measured, the WMS Kundin Measurements dialog box (shown in FIG. 20) will appear. The operator presses Calculate to have the WMS compute the Area and Volume and present them on screen. Pressing Ok saves and returns to the main dialog box shown in FIG. 6, or Cancel returns to the main dialog box without saving.

The formulas used in the calculation of Volume and Area are as follows:

AREA=[(North-South length)×(East-West width)]×0.785

VOLUME=[(North-South length)×(East-West width)×(Depth)]×0.327

Figures 20, 21:
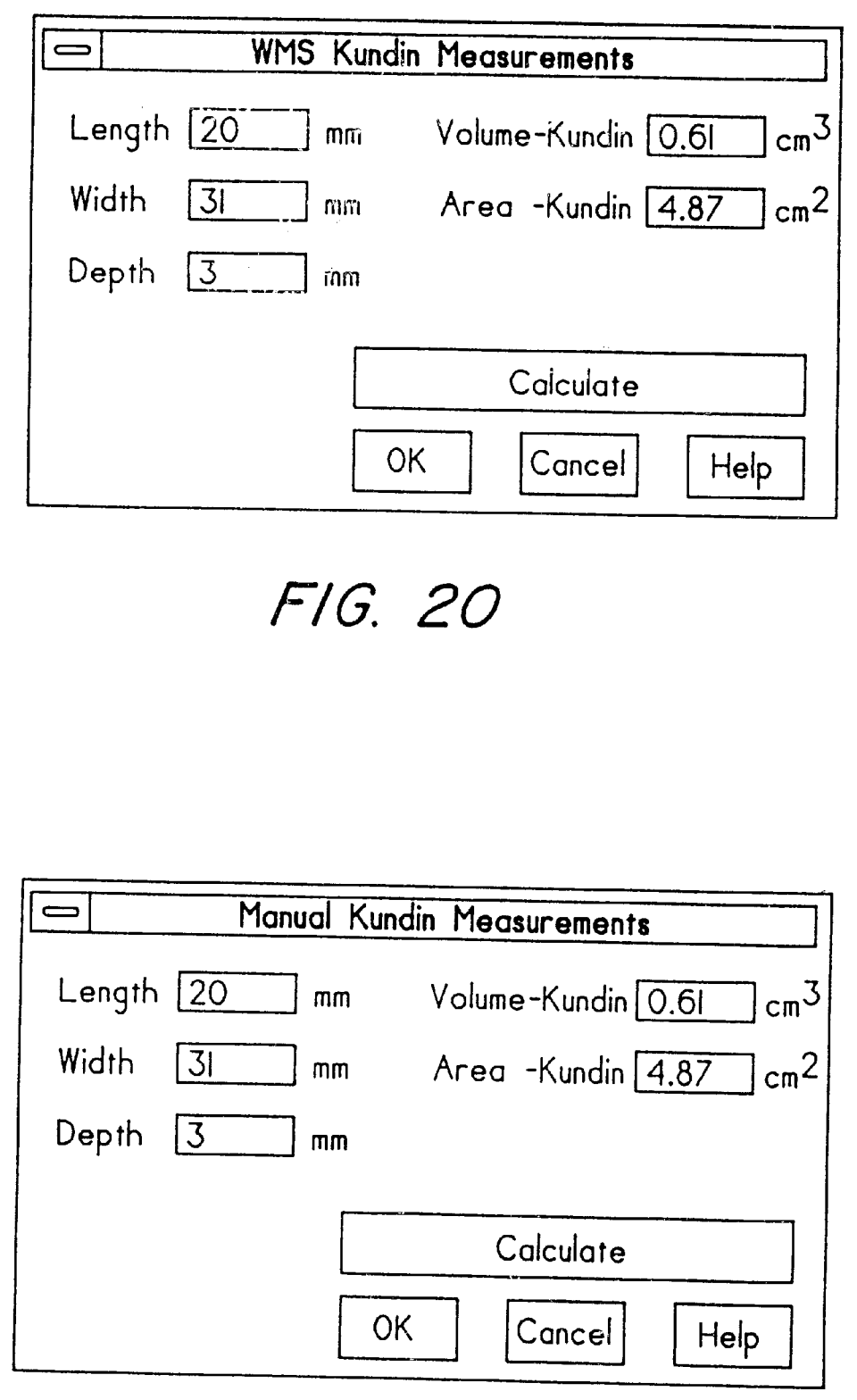

FIG. 21 is the manual Kundin measurement screen. Manual data entry selection involves entering the Length, Width and Depth (if applicable), as measured by using a conventional Kundin gauge. Once these three measurements are entered, the operator presses Calculate to obtain the calculated values for area and volume. These two values appear in the Area and Volume boxes as seen in FIG. 21.

LABS

The LABS button 15 allows the operator to either review a previously saved set of laboratory results for the current patient and selected wound or to enter a new set of laboratory results. To enter new data, the operator selects New Test in the test list 24 before pressing the LABS button 15. To review a saved set of laboratory results, the operator selects the test date on which the desired data was entered in the test list 24 before pressing the LABS button 15.

Once the LABS button 15 is pressed, the Labwork screen will appear as shown in FIG. 22. If the operator selected a New Test, the entry boxes will be blank, but if the operator chose to review a previously saved set of entries, these entries will appear in the entry boxes. Once the operator has entered the labwork data, they may select Ok to save the information, which will return the program to the main dialog box, or Cancel to abandon any entered or changed information but still return to the main dialog box. The Help button will provide help on the Labwork section of WMS.

WMS MEASUREMENTS

The WMS MEASUREMENTS button 16 directs the operator to the WMS Measurement screen shown in FIG. 23. The 3-D position coordinates are displayed realtime in a coordinate display area 50 in the upper-right hand corner of the measurement window. The measurement screen's button bank, located in the leftmost side of the window lets the operator control which type of measurements are to be performed. The draw area 60 is where the digitized points are displayed as they are entered and where the results will appear. A prompt area 62 provides instructions to the operator. The measurement window also has the standard set of buttons: Ok closes the measurement window and the prompt window below it and returns to the main dialog box in FIG. 6; Cancel also closes both windows and returns to the main dialog box but discards any data that may have been collected; and Help provides more details and instructions for measuring wound dimensions.

Figure 24:
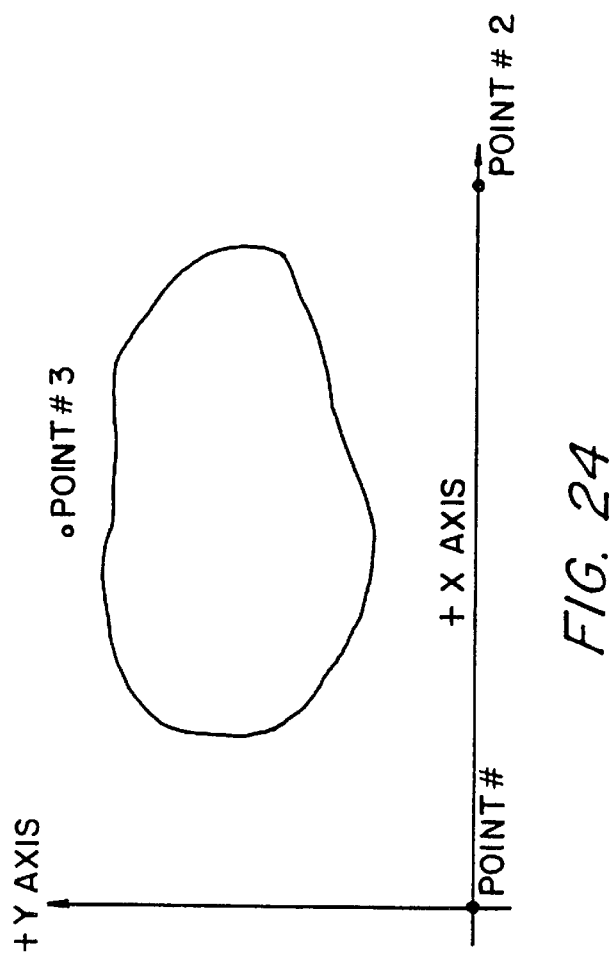
FIG. 24 is an illustration of the points defining the CMM coordinate system relative to a wound.

Before performing any measurements, a local coordinate system must be established for the wound that will be measured. The system will not let the operator proceed with data collection until after this is done. As shown in FIG. 24, the system prompts the operator to digitize three points. The first point will serve as a new origin, i.e. the (0,0) point for the coordinate system. The first point should be below (distally) and to the left of the wound to be measured, The second point will serve as a new X-axis. The second point should be below (distally) and to the right of the wound to be measured. The third point will serve to set up the X-Y plane, i.e. it indicates which flat surface will be measured. The third point should be somewhere above (proximally) the wound site. If the operator will be comparing wound measurements, an indelible marker should be used to mark the three points used to setup the coordinate system so that the coordinate system can be recreated from one test to another. This will ensure that the same data is compared from one test date to the next.

Once the wound coordinate system is established, the system is ready to begin gathering data. The buttons 51–57 provide access to various measurement and data management function. The functions associated with each button 51–57 are described below.

Perimeter Scans

The perimeter scans of a wound are always of great interest since they provide the examiner with valuable information. Surface area has long been recognized as a useful tool in evaluating wound healing when measured over time, however, acetate tracing (the most common method) has its disadvantages in that examiners must not only trace the outline of the wound opening onto the gridded acetate, but they must also estimate what the surface area of the wound opening is based on how many full and partial squares fall within tracing.

Figure 25:
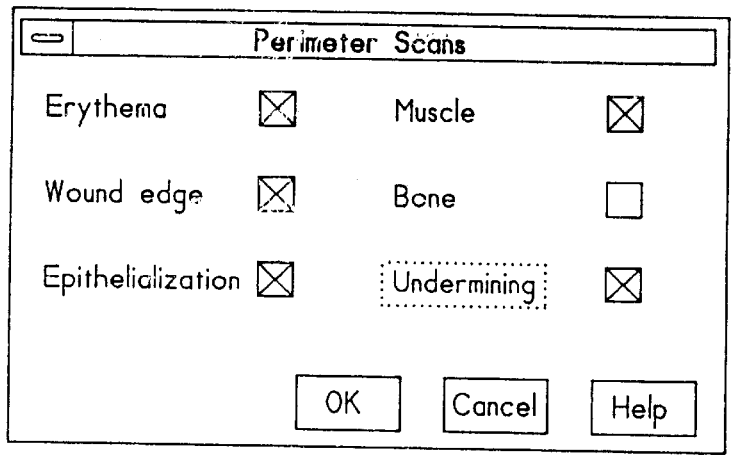
FIG. 25 is an illustration of a perimeter digitizing screen.

The WMS eliminates all this guesswork, and also gives examiners the choice of which scans they wish to examine. When the PERIM button 51 is selected a small dialog box appears, as shown in FIG. 25, requesting the operator to select which of the six available perimeter scans are to be performed. The available perimeter scans are erythema, wound edge, epithelialization, muscle, bone and undermining. The operator may select as many as desired by selecting the check box next to the perimeter type. When the operator has selected all the desired scans, the Ok button is pressed to record the selections and return to the measurement window shown in FIG. 23. Note that the standard Cancel and Help buttons are also present.

Upon return to the measurement window shown in FIG. 23, the operator is prompted (in the prompt window 62) to scan the first perimeter that was selected. For example, if Erythema, Wound Edge, and Muscle were selected as the perimeters to be performed, the operator is prompted to scan the perimeter of the Erythema. The scanning arm includes a first switch referred to as the front switch and a second switch referred to as the back switch. During a scan, the operator collects points with the front switch depressed. A starting point somewhere along the perimeter is selected, the probe tip is positioned on that point, and the front switch is depressed to begin taking points. As the probe tip is moved along the perimeter, the points that are digitized appear in the draw area 60 of the measurement window. When the perimeter scan is complete, the front switch is released to end the scan.

If the operator is not satisfied with some points, the operator may backup along the perimeter one point at a time until the point(s) to be repeated are reached by choosing the BACKUP button 55 as many times as necessary. The operator may then start collecting points from that point on as described above. Each time the operator presses the backup button, that point that was backed up over is erased from memory, and therefore must be redigitized to replace it.

Figure 26:
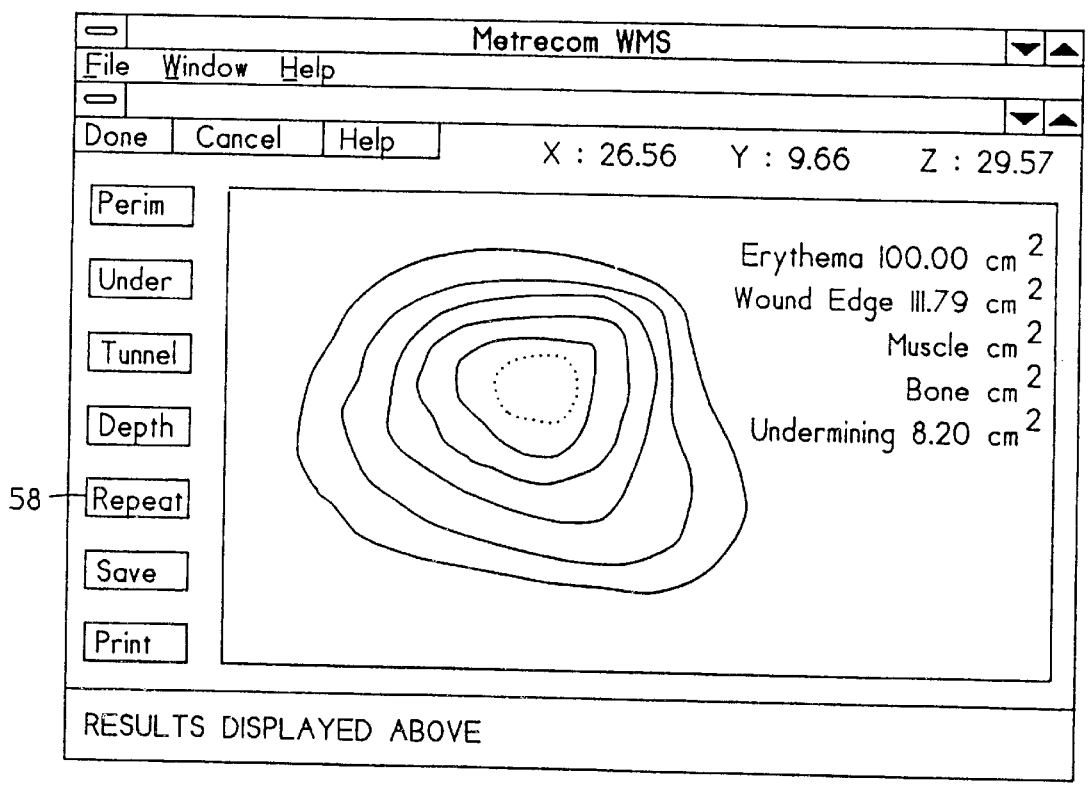
FIG. 26 is an illustration of a perimeter results screen.

If the operator is satisfied that valid points along the perimeter have been collected, the operator presses the back switch to accept this scan. Once the scan is completed and accepted, the operator is prompted to scan the perimeter of the next scan that had been selected in the perimeter selection dialog box (if any). Once the operator has completed and accepted the last scan in the selected perimeters, the area computations will take place, and the perimeter areas will be displayed in both graphical and numerical format, as seen in FIG. 26. If the operator desires to erase the whole scan and repeat it, the button that once displayed Backup will now display Repeat. Selecting the Repeat button allows the operator to re-scan the whole perimeter. The perimeter scan data can be saved by selecting the Save button 56. However, it is often more convenient to perform all the desired wound measurements and select the SAVE button 58 once the operator is ready to exit the measurement window.

Undermining

Figure 28:
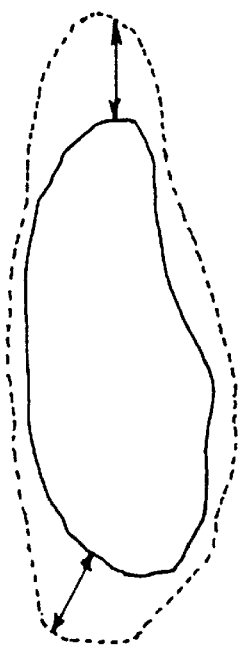
FIG. 28 is a top view of a wound illustrating wound undermining.
Figure 27:
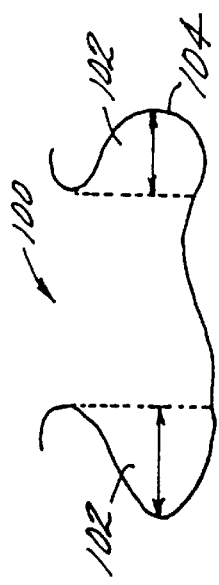
FIG. 27 is a side view of a wound illustrating wound undermining.

Undermining, or a concave intrusion of the wound underneath and beyond the wound opening, is a difficult measurement to take in the best of circumstances. Often, inaccessibility hinders the ability of the examiner to accurately gauge the amount of undermining which exists in a give wound. FIGS. 27 and 28 illustrate two different views of undermining. The undermining area 102 extends beyond the wound opening 100. The WMS can take these measurements in a matter of seconds. The WMS computes the location of the wound edge or opening 100, and then requires the examiner to digitize points (one or many) along the wound wall 104 where the undermining is occurring.

Figure 29:
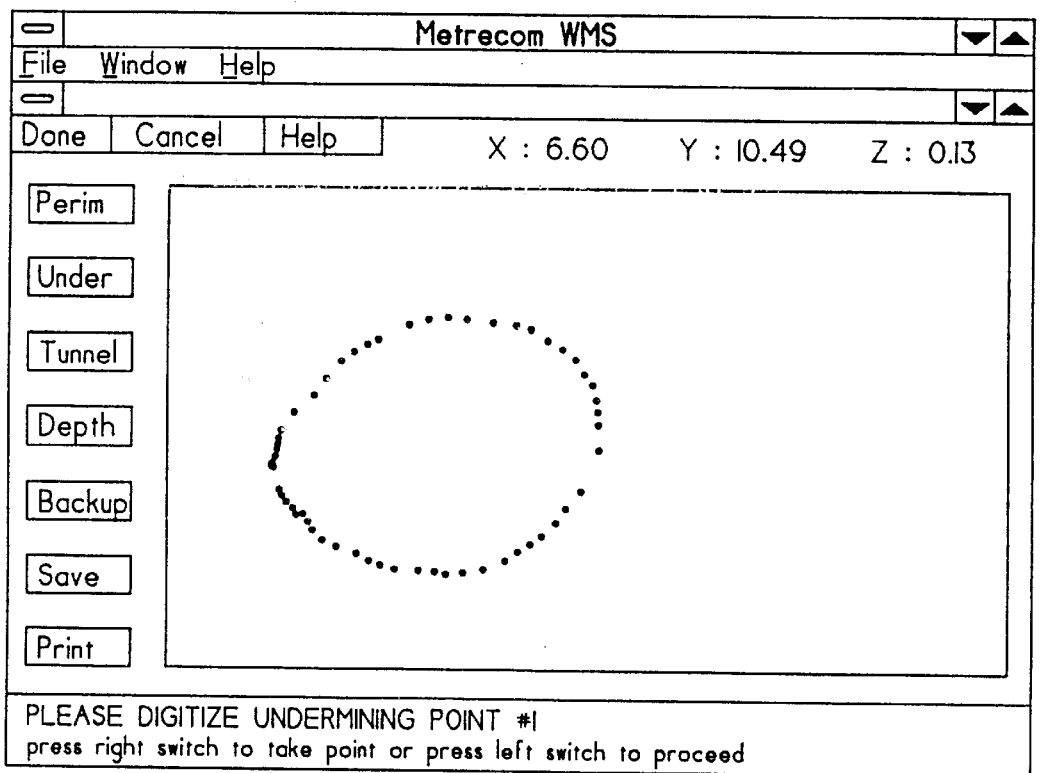
FIG. 29 is an illustration of a wound undermining digitizing screen.

The operator first chooses UNDER button 51, and is prompted to scan around the wound edge, if the wound perimeter has not already been measured in a perimeter scan as described above. The perimeter of the wound edge will then be displayed on screen, as shown in FIG. 29. For comparison, if the operator has a previously saved test which contained some undermining locations, these undermining locations will also be displayed so that the operator may take the new undermining points in the exact same locations and track the healing process.

Figure 30:
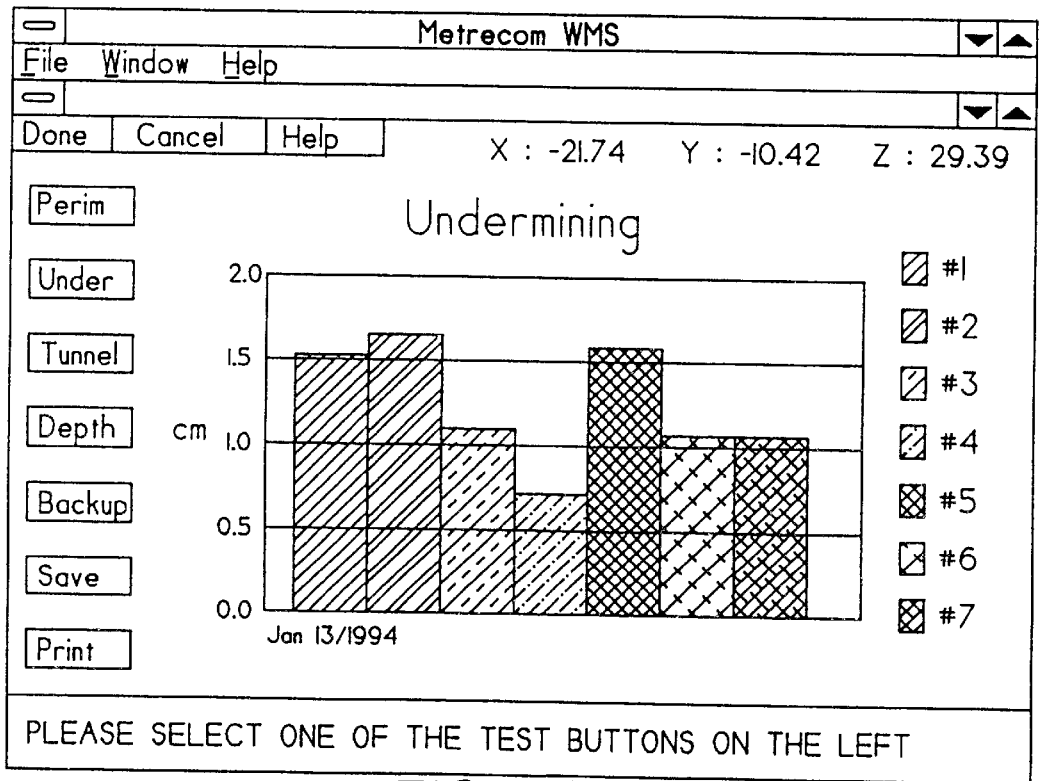
FIG. 30 is an illustration of an undermining results screen.

The operator positions the probe tip under the lip of the wound so that it touches the farthest edge of the wound wall, and digitizes a point by pressing the front switch to take the point, and the back switch to accept it. Up to 10 different points at different undermining locations may be taken. If less than 10 points are measured, the operator presses the back switch a second time to tell the program that this set of data is compete. Upon completion, the operator is presented with the computed data in graphical format, as seen in FIG. 30. The operator can print the graph if desired by selecting the print button 57, or wait and review it at a later date. As described above, the operator need not save the data immediately. In fact, it is usually more convenient to perform all measurements, then save the data by choosing the SAVE button 56 once the operator is ready to exit the measurement window.

Tunneling

Figure 32:
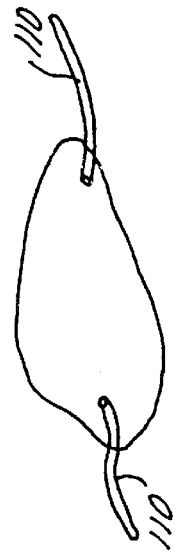
FIG. 32 is a top view of the wound including tunneling.
Figure 31:
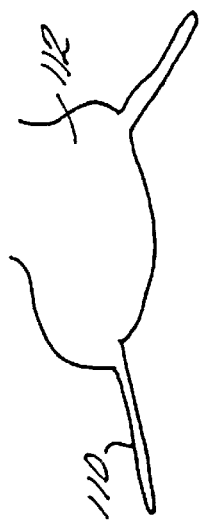
FIG. 31 is a side view of a wound including tunneling.

Tunneling, the formation of a tunnel-like intrusions from the wound wall leading away into the surrounding tissue, is, like undermining, a difficult parameter to measure. The WMS compares the entry point of the tunnel to the deepest point of the tunnel to obtain a length, and compares these two points to the perimeter of the wound itself to evaluate direction. FIG. 31 is a side view of tunneling showing a tunnel 110 extending away from the main region of the wound 112. FIG. 32 is a top view of the wound including tunnels 110.

Figure 33:
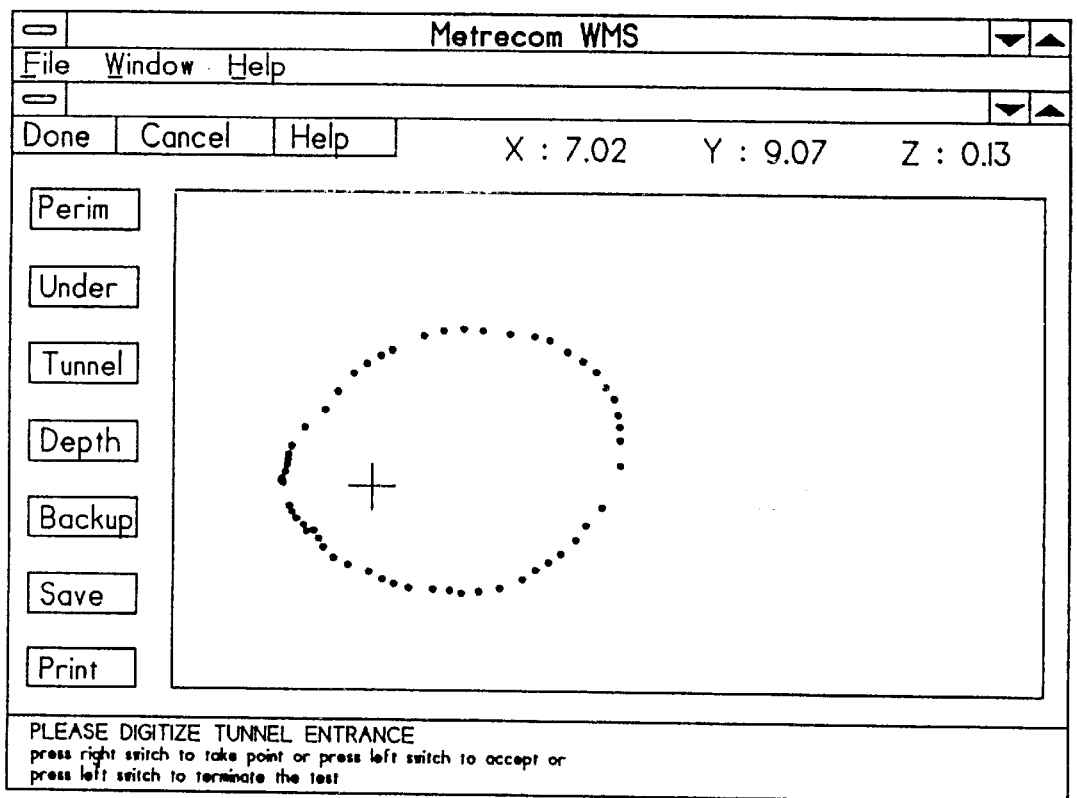
FIG. 33 is an illustration of a tunneling digitizing screen.

When the operator chooses the TUNNEL button 53, they are prompted to scan around the wound edge, if this has not already been done in a perimeter scan. The perimeter of the wound edge will then be displayed on screen, as shown in FIG. 33. For comparison, if a previously saved test exists which contains tunneling locations, the tunneling location will also be displayed so that the operator can digitize tunneling points in the exact same locations and track the healing progress.

Figure 34:
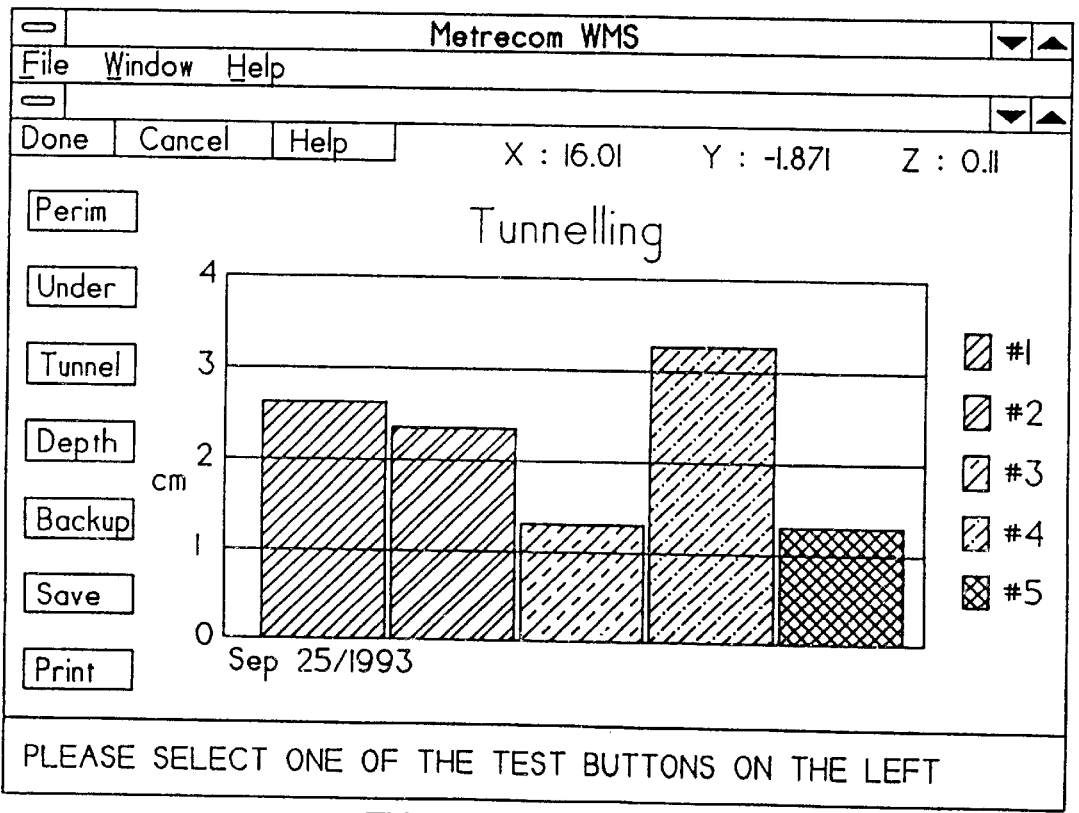
FIG. 34 is an illustration of a tunneling results screen.

To measure the tunneling locations, the operator positions the probe tip at the entrance of the tunnel, and digitizes a point by pressing the front switch to take the point, and the back switch to accept it. Then, the probe is inserted into the tunnel as far as it will go, and a point is digitized by pressing the front switch to take the point, and the back switch to accept it. This pair of points constitutes a tunnel. The operator may take up to 10 different pairs of points at different tunneling locations. If less than 10 pairs of points are measured, the operator must press the back switch a second time to tell the program that this set of data is complete. Upon completion, the computed data is displayed in graphical format, as shown in FIG. 34. The operator can print the graph if desired, or wait and review it at a later date. As described above, the operator need not save the data immediately. In fact, it is usually more convenient to perform all measurements, then save the data by choosing the SAVE button 56 once the operator is ready to exit the measurement window.

Depth

Depth is an important indicator of the healing process. The WMS automatically calculates the depth of the wound in up to 10 different locations. The depth is determined by comparing the position of a point digitized on the surface of the wound, to the height of the wound opening's edge as shown in FIGS. 35 and 36. The system automatically takes irregular surface heights into consideration when determining the depth, eliminating the guesswork in 'eye-balling' the average height of the wound edge.

When the operator chooses the DEPTH button 54, they are prompted to scan around the wound edge, if this has not already been done during a perimeter scan as described above. The perimeter of the wound edge will then be displayed on screen, as shown in FIG. 37. For comparison, if a previously saved test contains depth locations, the depth locations will also be displayed so that the operator may digitize the new depth points in the exact same locations and track the healing progress.

Figures 38, 39:
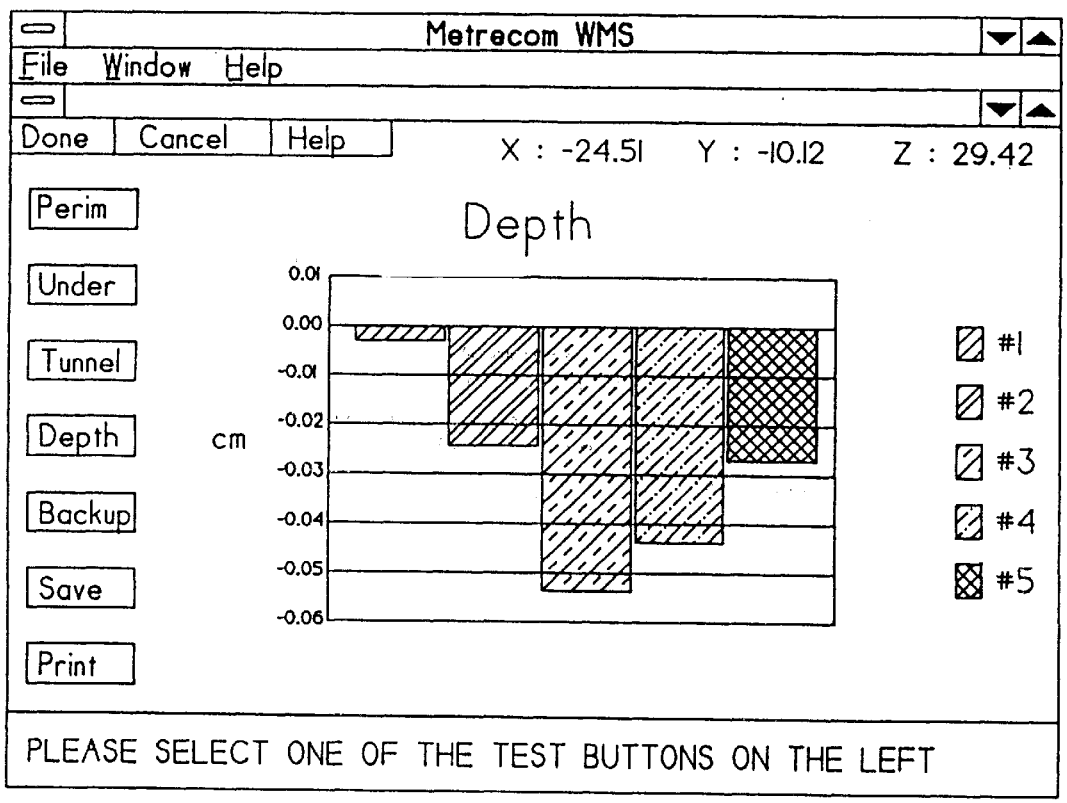
FIG. 38 is an illustration of a wound depth results screen.
FIG. 39 is an illustration of a review saved tests screen.

The depth measurements are made by positioning the probe tip at the bottom surface of the wound, and digitizing a point by pressing the front switch to take the point, and the back switch to accept it. Up to 10 different depth points at different locations maybe taken. If the operator chooses to take less than 10 points, the back switch is pressed a second time to tell the program that the set of data is complete. Upon completion, the computed depth data is presented in a graphical format, as seen in FIG. 38. The operator can print the graph if desired, or wait and review it at a later date. As described above, the operator need not save the data immediately. In fact, it is usually more convenient to perform all measurements, then save the data by choosing the SAVE button 56 once the operator is ready to exit the measurement window.

Save

The SAVE button 56 saves the collected data to a file so that it may be retrieved at a later date. The saved data is accessed by patient name and test date as will be described below.

Print

The PRINT button 57 allows the operator to send the graphical results to a printer. The print feature can be useful when performing a measurement, but the operator does not wish to save the data to disk. Pressing the PRINT button provides a hardcopy of the results.

REVIEW SAVED RESULTS

From the main dialog window shown in FIG. 6, selecting button 17 allows the operator to review saved tests quickly and conveniently. Immediately upon pressing the REVIEW SAVED TEST button 17, the program presents the Review Saved Tests screen shown in FIG. 39. To review a particular test, the operator selects both a patient record from patient list 200 and a wound location from wound list 210. Once this is done, the available saved test dates will appear in the saved test list 220. The operator may select more than one test date if they desire to compare similar tests.

The next step is to select which parts of the saved test(s) are to be reviewed. For example, a test performed on a certain date may contain, an ASSESSment, a KUNDIN calculation, a Norton SCORE, and a set of areas PERI-Neters. The operator may only wish to review the Kundin results. The right side of the Review Saved Tests dialog screen contains six different lists, each of which represents a different area of calculations: WMS Location displays 230, WMS Area displays 240, Lab displays 250, Assess displays 260, Score displays 270, and Kundin displays 280.

WMS Location displays 230 consist of the depth, tunneling, and undermining data.

WMS Area displays 240 consist of the wound perimeters.

Lab displays 250 consist of the labwork values.

Assess displays 260 consist of the numeric values in the three assessment dialog boxes.

Score displays 270 consist of the Norton, Gosnell, and Braden scores.

Figure 40:
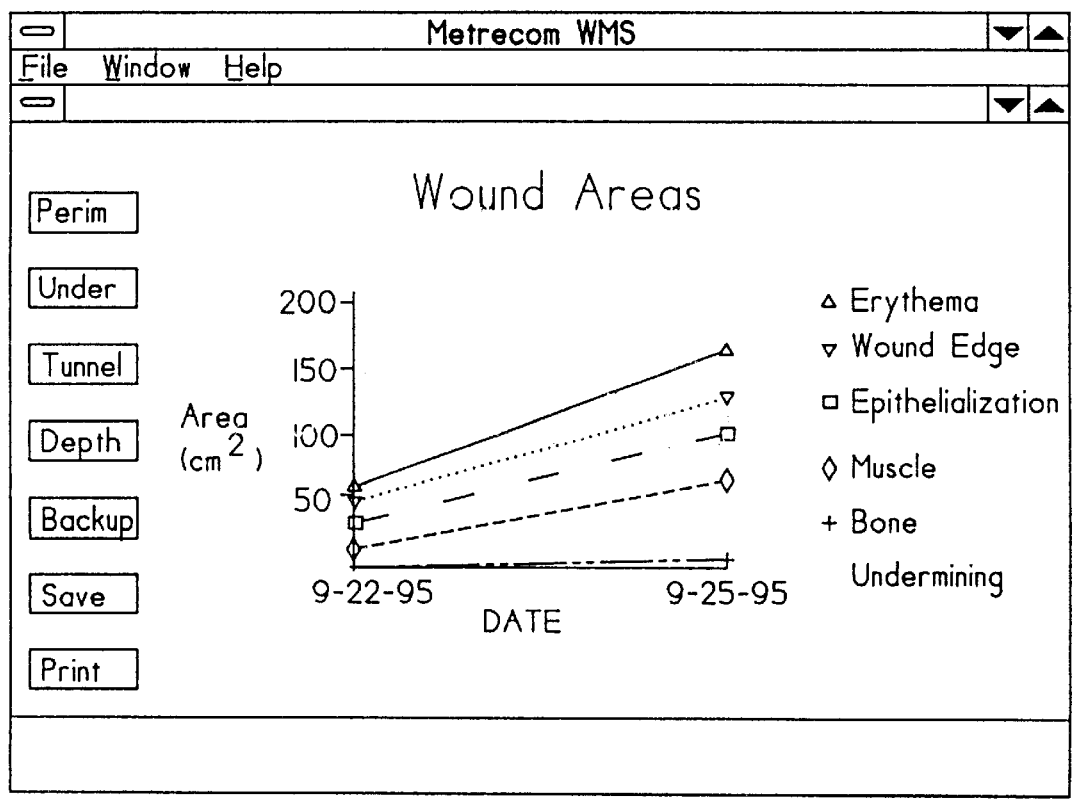
FIG. 40 is an illustration of a graphical display of saved wound data.

Kundin displays 280 consist of the manual and automatic Kundin values. The operator selects a test format from as many of the areas 230–280 as desired. When all the selections are made, the operator selects Ok to proceed. As soon as Ok is selected, the Review dialog box disappears, and the review windows (one for each area selected) will appear on screen. Multiple review windows may be tiled or overlapped as is known in the art. The data is presented in each window as either a bar graphs (if only one test date selected), or as line graphs (if multiple test dates selected). If the test date that you selected did not contain any data for a certain area, the graph will come out blank. A sample of a review window is shown in FIG. 40.

The probe on the end of the CMM 10 may measure three-dimensional wound parameters other than the wound location. For example, an oxygen or temperature probe may be installed at the end of the CMM to generate a three dimensional map of oxygenation or temperature. An exemplary CMM including a transducer for sensing a non-dimensional parameter is disclosed in U.S. Pat. No. 5,412,880, the entire contents of which are incorporated herein by reference. In addition, the database may store digital images of the wound to provide further information necessary to diagnosis.

The wound management system of the present invention provides the practitioner with a powerful tool for wound analysis. The CMM allows for precise measurement of a variety of wound parameters. These measured wound parameters, which may be combined with wound observations, are collected in a wound database. The wound data is then presented to the practitioner so that the progress of the wound healing may be easily tracked.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A wound management system comprising:
   a measuring device having a probe tip for contacting a patient and measuring a wound parameter and;
   a computer coupled to said measuring device, said computer including a database for storing said wound parameter wherein said wound parameter includes wound undermining.

2. A wound management system comprising:
   a measuring device having a probe tip for contacting a patient and measuring a wound parameter and;
   a computer coupled to said measuring device, said computer including a database for storing said wound parameter wherein said wound parameter includes wound tunneling.

3. A wound management system comprising:
   a measuring device having a probe tip for contacting a patient and measuring a wound parameter and;
   a computer coupled to said measuring device, said computer including a database for storing said wound parameter wherein said wound parameter includes at least one Kundin measurement.

4. The wound management system of claim 3 wherein a Kundin score is generated automatically based on said at least one Kundin by said computer based on a predetermined number of points identified by said measuring device.

5. A method for measuring and monitoring wounds of a patient, the method comprising:
   operating a measuring device having a probe tip for contacting a patient and measuring a wound parameter;
   collecting said wound parameter in a database stored in a computer; and
   displaying the wound parameter on a display device coupled to the computer wherein said wound parameter includes wound undermining.

6. A method for measuring and monitoring wounds of a patient, the method comprising:
   operating a measuring device having a probe tip for contacting a patient and measuring a wound parameter;
   collecting said wound parameter in a database stored in a computer; and
   displaying the wound parameter on a display device coupled to the computer wherein said wound parameter includes wound tunneling.

7. A method for measuring and monitoring wounds of a patient, the method comprising:
   operating a measuring device having a probe tip for contacting a patient and measuring a wound parameter;
   collecting said wound parameter in a database stored in a computer; and
   displaying the wound parameter on a display device coupled to the computer wherein said wound parameter includes at least one Kundin measurment.

8. The method of claim 7 wherein a Kundin score is generated automatically based on said at least one Kundin measurement based on.

9. A method for measuring and monitoring wounds of a patient, the method comprising:
   operating a measuring device having a probe end for measuring a wound parameter;
   collecting said wound parameter in a database stored in a computer; and
   displaying the wound parameter on a display device coupled to the computer wherein the display device displays in real time a location of the probe end.

10. The method of claim 9 further comprising identifying three dimensional location of wound points on the patient and said displaying step further comprising displaying wound points as the wound points are measured.

11. The method of claim 10 further comprising displaying previously measured wound points prior to obtaining additional wound points.

12. The method of claim 9 further comprising establishing a wound coordinate a system by measuring a predetermined number of points prior to measuring wound parameters.

13. The method of claim 9 wherein said wound parameter includes wound dimensional data.

14. The method of claim 9 wherein said operating step includes operating articulated arm.

15. The method of claim 9 wherein the measuring step includes contacting the patient with the probe end.

* * * * *

UNITED STATES PATENT AND TRADEMARK OFFICE
CERTIFICATE OF CORRECTION

PATENT NO. : 6,413,212 B1
APPLICATION NO. : 09/401244
DATED : July 2, 2002
INVENTOR(S) : Simon Raab It is certified that error appears in the above-identified patent and that said Letters Patent is hereby corrected as shown below:

Drawings
<u>Figure 14,</u>
Delete "Assit" and insert therefor -- Assist --.

Drawings
<u>Figure 15,</u>
Delete "Noisture" and insert therefor -- Moisture --.

Drawings
<u>Figure 16,</u>
Delete "Menbility" and insert therefor -- Mobility --.

<u>Title Page,</u>
Item (56) References Cited, insert -- Zahouani, et al., *Theoretical and experimental study of wound healing: application to leg ulcers,* Mar. 1992, pp. 234-239. vol. 30 No. 2 --,
Item (56) References Cited, insert -- Mignot, et al., *Image analysis and 3-D profilometry of the human skin surface,* Nov. 1986, pp. 1414-1417, vol. 3. --.

<u>Column 1,</u>
Line 9, after "5,957,837" insert -- , the --.

<u>Column 3,</u>
Line 65, after "46" delete "transgversely" and insert therefor -- transversely --.

<u>Column 4,</u>
Line 2, after "with" delete "an" and insert therefor -- A --,
Line 19, after "52." delete "An" and insert therefor -- A --,
Line 60, after "becomes" delete "and" and insert therefor -- an --.

<u>Column 6,</u>
Line 34, after "test" (second occurrence) delete "wag" and insert therefor -- was --,
Line 51, after "lower" delete "lib" and insert therefor -- limb --,
Line 65, after "hand" delete "comer" and insert therefor -- corner --.

<u>Column 7,</u>
Line 25, after "the" delete "operators" and insert therefor -- operator --.

UNITED STATES PATENT AND TRADEMARK OFFICE
CERTIFICATE OF CORRECTION

PATENT NO. : 6,413,212 B1
APPLICATION NO. : 09/401244
DATED : July 2, 2002
INVENTOR(S) : Simon Raab It is certified that error appears in the above-identified patent and that said Letters Patent is hereby corrected as shown below:

Column 8,
Line 54, after "hand" delete "comer" and insert therefor -- corner --.

Column 9,
Line 16, after "to" delete "setup" and insert therefor -- set up--.

Column 12,
Line 27, before "The" delete "Neters." and insert therefor -- Meters. --,
Line 49, after "either" delete "a".

Column 14,
Line 19 Claim 8, after "on" insert -- a predetermined number of wound points --,
Line 30 Claim 9, before "three" insert -- a --,
Line 40 Claim 12, after "coordinate" delete "a",
Line 42 Claim 45, after "operating" insert -- an --.

Signed and Sealed this

First Day of April, 2008

JON W. DUDAS
*Director of the United States Patent and Trademark Office*